United States Patent [19]

Clarke et al.

[11] Patent Number: 5,158,971
[45] Date of Patent: Oct. 27, 1992

[54] PHARMACEUTICAL COMPOUNDS

[75] Inventors: Trafford Clarke, Lightwater; David J. Steggles, Bracknell, both of England

[73] Assignee: Lilly Industries limited, Basingstoke, England

[21] Appl. No.: 705,191

[22] Filed: May 24, 1991

[30] Foreign Application Priority Data

Jun. 1, 1990 [GB] United Kingdom ............... 9012252

[51] Int. Cl.$^5$ ................... A61K 31/38; C07D 333/32
[52] U.S. Cl. ....................... 514/445; 549/65
[58] Field of Search ............ 549/65, 76, 77, 69; 514/445

[56] References Cited

U.S. PATENT DOCUMENTS

| | | |
|---|---|---|
| 4,382,929 | 5/1983 | Bradshaw et al. .............. 549/76 |
| 4,738,986 | 4/1988 | Kneen et al. . |
| 5,036,157 | 7/1991 | Kneen et al. . |

FOREIGN PATENT DOCUMENTS

| | | |
|---|---|---|
| 292699 | 11/1988 | European Pat. Off. . |
| WO90/12008 | 10/1990 | PCT Int'l Appl. . |

*Primary Examiner*—Alan Siegel
*Attorney, Agent, or Firm*—John C. Demeter; Leroy Whitaker

[57] ABSTRACT

A pharmaceutical compound of the formula

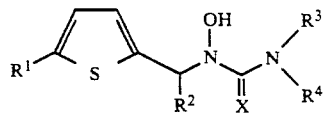

in which $R^1$ is halo-$C_{1-10}$ alkyl, $C_{1-10}$ alkylthio, halo-$C_{1-10}$ alkylthio or optionally substituted phenylthio, $R^2$ is hydrogen or $C_{1-4}$ alkyl, $R^3$ and $R^4$ are each hydrogen or $C_{1-4}$ alkyl, and X is oxygen or sulphur; and salts thereof.

4 Claims, No Drawings

PHARMACEUTICAL COMPOUNDS

This invention relates to novel compounds, their pharmaceutical use and methods of preparation.

The compounds of the invention have the formula

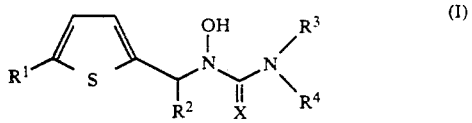

in which $R^1$ is halo-$C_{1-10}$ alkyl, $C_{1-10}$ alkylthio, halo-$C_{1-10}$ alkylthio or optionally substituted phenylthio, $R^2$ is hydrogen or $C_{1-4}$ alkyl, $R^3$ and $R^4$ are each hydrogen or $C_{1-4}$ alkyl, and X is oxygen or sulphur; and salts thereof.

The compounds of the invention inhibit the formation of leukotrienes and are indicated for use in diseases in which leukotrienes have a role, such as allergic disorders.

The invention particularly comprises a group of compounds of the above formula (I), excluding compounds in which X is oxygen, $R^3$ and $R^4$ are hydrogen and (1) $R^1$ is isopropylthio, tert. butylthio or phenylthio and $R^2$ is hydrogen, or (2) $R^1$ is methylthio, tert.-butylthio or phenylthio and $R^2$ is methyl; and salts thereof.

When $R^1$ is halo-$C_{1-10}$ alkyl, the alkyl group is substituted by one or more halogen, preferably chlor or fluoro. The alkyl group can be straight or branched and preferably contains from 3 to 8 carbon atoms. Preferably there are one to three halo substituents and they are in the $\omega$-position attached to the terminal position of the alkyl. A preferred group is one of the formula $CF_3(CH_2)_n$— where n is 2 to 7.

When $R^1$ is $C_{1-10}$ alkylthio, the alkyl group can be straight or branched chained and preferably contains from 3 to 8 carbon atoms. Preferred examples include pentylthio and hexylthio.

When $R^1$ is halo-$C_{1-10}$ alkylthio, the alkyl group is substituted by one or more halogen, preferably chloro or fluoro. The alkyl group can be straight or branched and preferably contains from 3 to 8 carbon atoms. Preferably there are one to three halo substituents and they are in the $\omega$-position attached to the terminal position of the alkyl. A preferred group is one of the formula $CF_3(CH_2)_nS$— where n is 2 to 7.

When $R^1$ is optionally substituted phenylthio and the phenyl group is substituted it can be substituted with one or more, preferably 1 to 3, substituents selected from for example halogen, nitro, cyano, carboxy, $C_{1-4}$ alkyl, $C_{1-4}$ alkoxy, $C_{1-4}$ alkylthio, halo-substituted $C_{1-4}$ alkyl and $C_{2-5}$ alkoxycarbonyl. Preferred substituents include chloro, bromo, nitro, carboxy, methyl, ethyl, t-butyl, methoxy, ethoxy, trifluoromethyl and ethoxycarbonyl. The group $R^1$ is preferably substituted phenylthio, and an especially preferred group is phenylthio with a single substituent selected from halogen, trifluoromethyl, $C_{1-4}$ alkoxy or $C_{1-4}$ alkyl group.

The groups $R^2$, $R^3$ and $R^4$ are the same or different and can be hydrogen or $C_{1-4}$ alkyl. Preferably $R^2$ is hydrogen or methyl, and one or both of $R^3$ and $R^4$ are hydrogen. The group X is preferably oxygen.

Preferred groups of compounds of formula (I) above are those in which (1) $R^1$ is halo-$C_{1-10}$ alkyl and (2) $R^1$ is halo-$C_{1-10}$ alkylthio.

A particularly preferred group of compounds is of the formula:

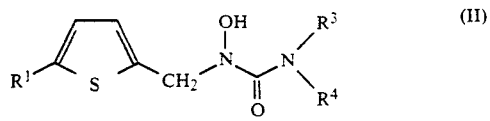

in which $R^1$ is substituted phenylthio and $R^3$ and $R^4$ are each hydrogen or $C_{1-4}$ alkyl. Preferably the phenylthio is substituted with a single substituent selected from halogen, trifluoromethyl, $C_{1-4}$ alkoxy or $C_{1-4}$ alkyl.

Examples of compounds according to the invention are:

1-hydroxy-1-[5-(3-trifluoromethylphenylthio)thien-2-ylmethyl]-urea 1-hydroxy-1-[5-(3-chlorophenylthio)thien-2-ylmethyl]urea 1-hydroxy-1-[5-(4-chlorophenylthio)thien-2-ylmethyl]urea 1-hydroxy-1-[5-(2-chlorophenylthio)thien-2-ylmethyl]urea 1-hydroxy-1-[5-(3,4-dichlorophenylthio)thien-2-ylmethyl]urea 1-hydroxy-1-[5-(4-methoxyphenylthio)thien-2-ylmethyl]urea 1-hydroxy-1-[5-(4-tert-butylphenylthio)thien-2-ylmethyl]urea.

It will be appreciated that the compounds of the invention can contain one or more asymmetric carbon atom which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form.

It is, of course, possible to prepare salts of the compounds of the invention because of the presence of the acidic hydroxyl group. Such salts are included in the invention. They can be any of the well known base addition salts. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

There may in addition be other salt-forming groups on, for example, a phenyl substituent, providing both base and acid addition salts. Moreover, the terminal amino group provides an opportunity for the formation of acid addition salts such as salts derived from nontoxic inorganic acids, for example, hydrochloric acid, nitric acid, phosphoric acid, sulphuric acid, hydrobromic acid, hydroiodic acid and phosphorous acid, as well as salts derived from non-toxic organic acids such as aliphatic mono- and dicarboxylic acids, especially fumaric acid, phenyl-substituted alkanoic acids, hydroxyalkanoic and hydroxyalkandioic acids, aromatic acids, aliphatic and aromatic sulphonic acids.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

The invention also comprises a process for producing compounds of the formula (I) above, which comprises (a) reacting a compound of the formula

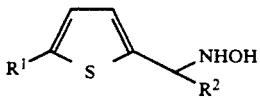
(III)

in which $R^1$ and $R^2$ have the values defined above, with an isocyanate or isothiocyanate, to give a compound of formula (I) in which X is O or S, respectively, and $R^3$ and $R^4$ are both hydrogen, or (b) reacting a compound of the formula

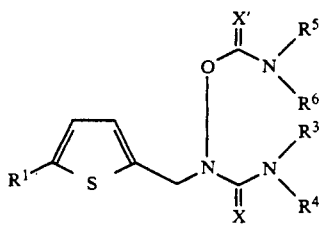
(IV)

in which $R^1$, $R^2$ and X have the values defined above, $R^3$ and $R^4$ are each $C_{1-4}$ alkyl, $X^1$ is oxygen or sulphur and $R^5$ and $R^6$ are each $C_{1-4}$ alkyl, with a base to give a compound of formula (I) in which $R^3$ and $R^4$ are each $C_{1-4}$ alkyl.

Reaction step (a) is preferably carried out in an organic solvent such as for example 1,4-dioxan, and at a temperature of from 20° C. to 100° C. The isocyanate and isothiocyanates are preferably salts having a good leaving group, and examples are trimethylsilylisocyanate and trimethylsilylisothiocyanate.

The hydroxylamine intermediate compounds of formula (III) are readily prepared by methods known in the art. Beginning with thiophene the thio-substituent can be introduced by reaction with the appropriate sulphenyl halide, or the haloalkyl substituent is introduced by alkylation. The product is acylated to give a compound of the formula:

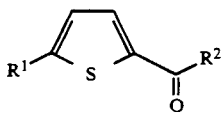

The oxime product formed by reacting this compound with hydroxylamine can then be reduced using a suitable reducing agent such as sodium cyanoborohydride to give the compound of formula (III).

Reaction step (b) is preferably carried out in an organic solvent such as an alcohol for example isopropanol, and at a temperature of from 0° C. to 50° C. The reaction of the diacyl derivative (III) with base causes the removal of the more labile group. The base employed may be any suitable reagent and examples include alkaline hydroxides such as sodium, potassium or lithium hydroxides.

Compounds of formula (IV) can readily be prepared by acylation of the hydroxylamine compounds of formula (III) by conventional means.

The compounds of the invention inhibit 5-lipoxygenase product formation as shown in the test described by J. Harvey and D. J. Osborne, J. Pharmacological Methods 9, 147-155 (1983), and the compounds of the invention in the following Examples have an $IC_{50}$ of less than 3 $\mu$M. They are thus indicated for the therapeutic treatment of diseases in which leukotrienes are implicated. These include immediate hypersensitivity diseases, allergic reactions of the pulmonary system, for example, in lung disorders such as extrinsic asthma and industrial asthmas and in other inflammatory disorders associated with acute or chronic infectious diseases such as allergic skin diseases, ectopic and atopic eczemas, psoriasis, contact hypersensitivity and antioneurotic oedema, bronchitis, cystic fibrosis and rheumatic fever. Furthermore, owing to their inhibition of leukotriene formation, the compounds have potential activity against a wide range of inflammatory diseases, and are also indicated for use in cancer treatment.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. When the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, aerosols, as a solid or in a liquid medium, ointments containing, for example, up to 10% by weight of the active compound, soft and hard gelatin capsules, suppositories, injection solutions and suspensions and sterile packaged powders. For administrations by inhalation, particular forms of presentation include aerosols, atomisers and vaporisers.

Some examples of suitable carriers are lactose, dextrose, sucrose, sorbitol, mannitol, starch, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

When the compotitions are formulated in unit dosage form, it is preferred that each unit dosage form contains from 10 mg to 1000 mg, more usually 25 to 500 mg, of the active ingredient. The term "unit dosage form" refers to physically discrete units suitable as unit dosage for human subjects and animals, each unit containing a predetermined quantity of active material calculated to produce the desired therapeutic effect, in association with the required pharmaceutical carrier.

The compounds are effective over a wide dosage range and for example dosages per day will normally fall within the range of 0.5 to 50 mg/kg and in the treatment of adult humans, more usually in the range of from 1 to 20 mg/kg. However, it will be understood that the amount of the compound actually aministered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention.

EXAMPLE 1

2-(Phenylthio)thiophene

To a suspension of N-chlorosuccinimide (7.8 g) in benzene (30 ml) was added dropwise, a solution of thiophenol (5.51 g) in benzene (20 ml) at room temperature. After 1 hour, the suspension was filtered, the filter pad washed with benzene and the filtrate evaporated under reduced pressure to give an orange oil. The oil was dissolved in dry tetrahydrofuran (20 ml) and added dropwise to a solution of 2-thienyl-lithium (prepared by the addition of n-butyllithium (20 ml, 2.5M) to thiophene (4.2 g) in dry tetrahydrofuran (30 ml) at −15° C. under nitrogen and stirred for 2 hours) at −15° C. under $N_2$. The solution was stirred for 1 hour, allowed to warm to room temperature and stirred overnight. The reaction mixture was poured on to ice, extracted with ether (3×100 ml), dried over $MgSO_4$ and evaporated under reduced pressure to give a brown oil. The oil was flash chromatographed on a Sorbsil C60-40/60H column using petroleum ether (40°-60° C.) to give a colourless oil, b.p. 161° C./20 mm pressure.

The following compounds were prepared by a similar method:
2-(3-Trifluoromethylphenylthio)thiophene
2-(3-Chlorophenylthio)thiophene
2-(4-Chlorophenylthio)thiophene
2-(2-Chlorophenylthio)thiophene
2-(3,4-Dichlorophenylthio)thiophene
2-(4-Methoxyphenylthio)thiophene
2-(4-tert-Butylphenylthio)thiophene
2-n-Pentylthiothiophene
2-(6,6,6-Trifluorohexylthio)thiophene

EXAMPLE 2

5-(Phenylthio)thiophene-2-aldehyde

To a solution of 2-phenylthiothiophene (3.87 g) in dry tetrahydrofuran (50 ml) at −30° C. under $N_2$, was added dropwise, n-butyllithium (8.0 ml, 2.5M) and the solution left to stir at −30° C. for 2 hours. Dry dimethylformamide (2.32 ml) was then added and the solution allowed to stir at −30° C. for a further hour, allowed to warm to room temperature and stirred overnight. The reaction mixture was quenched with 2N HCl (50 ml), extracted with ether (2×50 ml), dried over $MgSO_4$ and evaporated under reduced pressure to give an orange oil. The oil was flash chromatographed on a Sorbsil C60-40/60H column using 20% ether-hexane to give a pale yellow oil.

The following compounds were prepared in a similar manner:
5-(3-Trifluoromethylphenylthio)thiophene-2-aldehyde
5-(3-Chlorophenylthio)thiophene-2-aldehyde
5-(4-Chlorophenylthio)thiophene-2-aldehyde
5-(2-Chlorophenylthio)thiophene-2-aldehyde
5-(3,4-Dichlorophenylthio)thiophene-2-aldehyde
5-(4-Methoxyphenylthio)thiophene-2-aldehyde
5-(4-tert-Butylphenylthio)thiophene-2-aldehyde
5-n-Pentylthiothiophene-2-aldehyde
5-(6,6,6-Trifluorohexylthio)thiophene-2-aldehyde

EXAMPLE 3

2-Acetyl-5-(3-trifluoromethylphenylthio)thiophene

To a solution of 2-(3-trifluoromethylphenylthio)thiophene (4.0 g) in dry tetrahydrofuran (30 ml) at −30° C. under nitrogen, was added dropwise n-butyllithium (9.2 ml, 2.5M) and the solution left to stir at −30° C. for 2 hours. Dimethylacetamide (2.8 ml) was then added dropwise and the reaction mixture stirred at −30° C. for a further hour, allowed to warm to room temperature and stirred over night. The reaction mixture was quenched with 2N HCl (100 ml), extracted with ether (2×100 ml), dried over $MgSO_4$ and evaporated to give a brown oil. The oil was flash chromatographed on a Sorbsil C60-40/60H column using 30% ether-hexane to give a colourless oil which crystallised on standing.

The following compounds were prepared by a similar method:
2-Acetyl-5-(3-chlorophenylthio)thiophene.

EXAMPLE 4

N-(5-Phenylthiothien-2-ylmethyl)oxime

To a solution of the aldehyde (2.5 g) in dry pyridine (25 ml) was added hydroxylamine hydrochloride (0.84 g) and the solution stirred at room temperature for 4 hours. The solution was diluted with ether (100 ml), washed with 2N HCl (3×50 ml), dried over $MgSO_4$ and evaporated under reduced pressure to give a pale yellow solid. The solid was flash chromatographed on a Sorbsil C60-40/60H column using 30% ether-hexane to give a pale cream solid.

The following compounds were prepared by a similar method:
N-[5-(3-Trifluoromethylphenylthio)thien-2-ylmethyl]oxime
N-[5-(3-Chlorophenylthio)thien-2-ylmethyl]oxime
N-[5-(4-Chlorophenylthio)thien-2-ylmethyl]oxime
N-[5-(2-Chlorophenylthio)thien-2-ylmethyl]oxime
N-[5-(3,4-Dichlorophenylthio)thien-2-ylmethyl]oxime
N-[5-(4-Methoxyphenylthio)thien-2-ylmethyl]oxime
N-[5-(4-tert-Butylphenylthio)thien-2-ylmethyl]oxime
N-[5-n-Pentylthothien-2-ylmethyl]oxime
N-[5-(6,6,6-Trifluorohexylthio)thien-2-ylmethyl]oxime
N-[5-(3-Trifluoromethylphenylthio)thien-2-ylethyl]oxime
N-[5-(3-Chlorophenylthio)thien-2-ylethyl]oxime

EXAMPLE 5

N-(5-Phenylthiothien-2-ylmethyl]hydroxylamine

To a solution of N-(5-phenylthiothien-2-ylmethyl)oxime (2.5 g) in glacial acetic acid (25 ml) was carefully added sodium cyanoborohydride (1.0 g) and the reaction mixture was allowed to stir at room temperature for six hours. 2N Sodium hydroxide solution was added carefully to neutralisation, the aqueous suspension extracted with ether (2×100 ml), dried over $MgSO_4$ and evaporated under reduced pressure to give a pale brown oil.

The following compounds were prepared by a similar method:
N-[5-(3-Trifluoromethylphenylthio)thien-2-ylmethyl]-hydroxylamine N-[5-(3-Chlorophenylthio)thien-2-ylmethyl]hydroxylamine N-[5-(4-Chlorophenylthio)thien-2-ylmethyl]hydroxylamine N-[5-(2-Chlorophenylthio)thien-2-ylmethyl]hydroxylamine N-[5-(3,4-Dichlorophenylthio)thien-2-ylmethyl]hydroxylamine N-[5-(4-Methoxyphenylthio)thien-2-ylmethyl]hydroxylamine N-[5-(4-tert-Butylphenylthio)thien-2-ylmethyl]hydroxylamine N-[5-n-Pentylthiothien-2-ylmethyl]hydroxylamine N-[5-(6,6,6-Trifluorohexylthio)thien-2-ylmethyl]hydroxylamine N-[5-(3-Trifluoromethylphenylthio)thien-2-ylethyl]hydroxylamine N-[5-(3-Chlorophenylthio)thien-2-ylethyl]hydroxylamine

EXAMPLE 6

1-Hydroxy-1-(5-phenylthiothien-2-ylmethyl)urea

To a solution of N-(5-phenylthiothien-2-ylmethyl)-hydroxylamine (2.5 g) in dioxan (50 ml) at room temperature under nitrogen, was added trimethylsilylisocyanate (2.42 g) and the resulting solution stirred for 1 hour, quenched with saturated aqueous ammonium chloride, extracted with ether (2×100 ml), dried over MgSO4 and evaporated under reduced pressure to give a yellow oil. The oil was flash chromatographed on a Sorbsil C60-40/60H column using ether to give a white solid, recrystallised from ether/petroleum ether to give a white crystalline solid m.p. 127°–129° C.

The following compounds were prepared by a similar method:

1-Hydroxy-1-[5-(3-trifluoromethylphenylthio)thien-2-ylmethyl]-urea(ether-petroleum ether) m.p. 106°–108° C.

1-Hydroxy-1-[5-3-chlorophenylthio)thien-2-ylmethyl]urea (ether-petroleum ether) m.p. 128°–129° C.

1-Hydroxy-1-[5-(4-chlorophenylthio)thien-2-ylmethyl]urea (ether-petroleum ether) m.p. 158°–160° C.

1-Hydroxy-1-[5-(2-chlorophenylthio)thien-2-ylmethyl]urea (ether-petroleum ether) m.p. 118°–123° C.

1-Hydroxy-1-[5-(3,4-dichlorophenylthio)thien-2-ylmethyl]urea (ether-petroleum ether) m.p. 74° C.

1-Hydroxy-1-[5-(4-methoxyphenylthio)thien-2-ylmethyl]urea (ether-petroleum ether) m.p. 137°–139° C.

1-Hydroxy-1-[5-(4-tert-butylphenylthio)thien-2-ylmethyl]urea (ether-petroleum ether) m.p. 130° C.

1-Hydroxy-1-[5-n-pentylthiothien2-ylmethyl]urea (ether-petroleum ether) m.p. 99°–100° C.

1-Hydroxy-1-[5-(6,6,6-trifluorohexylthio)thien-2-ylmethyl]urea

EXAMPLE 7

1-Hydroxy-1-[5-(3-trifluoromethylphenylthio)thien-2-ylethyl]-urea

To a solution of N-[5-(3-trifluoromethylphenylthio)-thien-2-ylethyl]hydroxylamine (7.6 g) in dioxan (70 ml) at room temperature under nitrogen, was added trimethylsilylisocyanate (5.48 g) and the reaction mixture stirred for 2 hours. The solution was quenched with saturated aqueous ammonium chloride, extracted with ether (2×100 ml), dried over MgSO4, evaporated under reduced pressure to give a yellow oil. The oil was flash chromatographed on a Sorbsil C60-40/60H column using ether to give a white solid, recrystallised from ether-petroleum ether, m.p. 124°–126° C.

The following compounds were prepared by a similar method:

1-Hydroxy-1-[5-(3-chlorophenylthio)thien-2-ylethyl]urea (ether-petroleum ether) m.p. 165°–167° C.

EXAMPLE 8

1-Hydroxy-1-[5-n-pentylthiothien-2-ylmethyl]thio urea

To a solution of N-[5-n-pentylthiothien-2-ylmethyl]-hydroxylamine (4.36 g) in dioxan (60 ml) at room temperature under nitrogen, was added trimethylsilylisothiocyanate (3.11 g) and the solution heated at reflux for 1 hour. The cooled solution was quenched with saturated aqueous ammonium chloride, dried over MgSO4 and evaporated under reduced pressure to give a brown oil. The oil was flash chromatographed on a Sorbsil C60-40/60H column using ether to give a pale yellow solid, recrystallized from n-hexane to give a cream crystalline solid m.p. 112°–114° C.

EXAMPLE 9

2-(4-Chlorophenylthio)thiophene

To a suspension of N-chlorosuccinimide (10.78 g) in dry toluene (45 ml) was added dropwise, a solution of 4-chlorothiophenol (9.84 g) in dry toluene (35 ml) at room temperature. After 1 hour, the suspension was filtered, the filter pad washed with toluene (100 ml) and the filtrate evaporated under reduced pressure to give an orange oil. The oil was dissolved in dry tetrahydrofuran (40 ml) and added dropwise to a solution of 2-thienyllithium (prepared by the addition of n-butyllithium (27.2 ml, 2.5M) to thiophene (5.72 g) in dry tetrahydrofuran (60 ml) at −15° C. under nitrogen and stirred for 2 hours) at −15° C. under nitrogen. The solution was stirred for 1 hour, allowed to warm to room temperature and stirred overnight. The reaction mixture was poured onto ice, extracted with ether (3×100 ml), dried over MgSO4 and evaporated under reduced pressure to give a brown oil. The oil was flash chromatographed on a Sorbsil C60-40/60H column using petroleum ether (40°–60° C.) to give a colourless oil.

EXAMPLE 10

5-(4-Chlorophenylthio)thiophene-2-aldehyde

To a solution of 2-(4-chlorophenylthio)thiophene (9.8 g) in dry tetrahydrofuran (75 ml) at −30° C. under nitrogen, was added dropwise, n-butyllithium (17.4 ml, 2.5M) and the solution left to stir at −30° C. for 2 hours. Dry dimethylformamide (5.1 ml) was then added and the solution allowed to stir at −30° C. for a further hour, warmed to room termperature and stirred overnight. The reaction mixture was poured onto 2N hydrochloric acid (75 ml), extracted with ether (2×100 ml), dried over MgSO4 and evaporated under reduced pressure to give a brown oil. The oil was flash chromatographed on a Sorbsil C60-40/60H column using 25% ether-hexane to give an orange oil.

EXAMPLE 11

N-[5-(4-Chlorophenylthio)thien-2-ylmethyl]oxime

To a solution of 5-(4-chlorophenylthio)thiophene-2-aldehyde (8.1 g) in dry pyridine (50 ml) was added hydroxylamine hydrochloride (2.2 g) and the solution stirred at room temperature for 5 hours. The solution was diluted with ether (200 ml), washed with 2N hydrochloric acid (3×100 ml), dried over MgSO$_4$ and evaporated under reduced pressure to give an orange solid. The solid was flash chromatographed on a Sorbsil C60-40/60H column using 30% ether-hexane to give a yellow solid.

EXAMPLE 12

N-[5-(4-Chlorophenylthio)thien-2-ylmethyl]hydroxy amine

To a solution of N-[5-(4-chlorophenylthio)thien-2-ylmethyl]oxime (7.9 g) in glacial acetic acid (75 ml) was added carefully sodium cyano borohydride (2.85 g) and the reaction mixture was allowed to stir at room temperature for 6 hours. 2N Sodium hydroxide solution was added carefully to neutralisation, the aqueous suspension extracted with ether (2×100 ml), dried over MgSO$_4$ and evaporated under reduced pressure to give a pale yellow-brown oil.

EXAMPLE 13

1-Hydroxy-1-[5-(4-chlorophenylthio)thien-2-ylmethyl]urea

To a solution of N-[5-(4-chlorophenylthio)thien-2-ylmethyl]hydroxylamine (6.65 g) in dioxan (100 ml) at room temperature under nitrogen, was added trimethylsilylisocyanate (4.25 g) and the resulting solution stirred for 2 hours, poured onto saturated aqueous ammonium chloride, extracted with ether (2×100 ml), dried over MgSO$_4$ and evaporated under reduced pressure to give a yellow oil. The oil was flash chromatographed on a Sorbsil C60-40/60H column using ether to give a white solid. Recrystallised from ether/petroleum ether (40°-60° C.) to give a white crystalline solid m.p. 158°-160° C.

EXAMPLE 14

2-(6,6,6-Trifluorohexyl)thiophene

To a solution of thiophene (4.2 g) in dry tetrahydrofuran (25 ml) at −15° C. under nitrogen, was added n-butyllithium (20 ml, 2.5M) dropwise and the solution stirred at −15° C. for 2 hours. The solution was then cooled to −78° C. and 6,6,6-trifluorohexylbromide (10.95 g) in dry tetrahydrofuran (20 ml) was added and solution stirred at −78° C. for 1 hour, allowed to warm to room temperature and stirred overnight. The reaction mixture was poured onto ice, extracted with ether (2×75 ml), dried over MgSO$_4$ and evaporated under reduced pressure to give a brown oil. The oil was distilled under reduced pressure to give a colourless oil, b.p. 66° C./20 mm.

EXAMPLE 15

5-(6,6,6-Trifluorohexyl)thiophene-2-aldehyde

To a solution of 2-(6,6,6-trifluorohexyl)thiophene (3.33 g) in dry tetrahydrofuran (30 ml) at −25° C. under nitrogen, was added n-butyllithium (8.2 ml, 2.5M) dropwise and the solution stirred at −25° C. for 2 hours. Dry dimethylformamide (2.34 ml) was then added dropwise and the solution stirred for a further hour, allowed to warm to room temperature and stirred for half hour. The reaction mixture was poured onto 2N hydrochloric acid (100 ml), extracted with ether (2×100 ml), dried over MgSO$_4$ and evaporated under reduced pressure to give a brown oil. The oil was distilled under reduced pressure to give a yellow oil b.p. 114° C./1 mm.

Similarly prepared using dimethylacetamide instead of dimethylformamide was:

5-(6,6,6-Trifluorohexyl)thien-2-ylmethylketone.

EXAMPLE 16

N-[5-(6,6,6-Trifluorohexyl)thien-2-ylmethyl]oxime

To a solution of 5-(6,6,6-trifluorohexyl)thiophene-2-aldehyde (2.94 g) in pyridine (25 ml) at room temperature, was added hydroxylamine hydrochloride (1.24 g) and the solution stirred at room temperature overnight. Ether (100 ml) was added and the solution washed with 2N hydrochloric acid (3×50 ml), dried over MgSO$_4$ and evaporated under reduced pressure to give a yellow solid.

Similarly prepared was:

N[1-{5-(6,6,6-Trifluorohexyl)thien-2-yl}ethyl]oxime.

EXAMPLE 17

N-[5-(6,6,6-Trifluorohexyl)thien-2-ylmethyl]hydroxylamine

To a solution of N-[5-(6,6,6-trifluorohexyl)thien-2-ylmethyl]oxime (3.09 g) in glacial acetic acid (30 ml) was carefully added sodium cyanoborohydride (4.4 g) and the solution allowed to stir at room temperature for 4 hours. Sodium hydroxide solution (2N) was added carefully to neutralisation, the aqueous solution extracted with ether (3×75 ml), dried over MgSO$_4$ and evaporated under reduced pressure to give a pale yellow oil.

Similarly prepared was:

N-[1-{5-(6,6,6-Trifluorohexyl)thien-2-yl}ethyl]hydroxylamine.

EXAMPLE 18

1-Hydroxy-1-[5-(6,6,6-trifluorohexyl)thien-2-yl methyl]urea

To a solution of N-[5-(6,6,6-trifluorohexyl)thien-2-ylmethyl]hydroxylamine (1.4 g) in dioxan (50 ml) under nitrogen with stirring, was added trimethylsilyl isocyanate (1.42 ml) and the reaction mixture stirred for 1 hour, poured onto 2N hydrochloric acid (100 ml), extracted with ether (2×100 ml), dried over magnesium sulphate and evaporated under reduced pressure to give a pale yellow oil. The oil was flash chromatographed on a Sorbsil C60-40/60H column using 4:1 hexane/ethyl acetate to give a white solid. Recrystallised from ether/petroleum ether (40°-60° C.) to give a white crystlline solid m.p. 94° C.

Similarly prepared was:

1-Hydroxy-1-[1-{5-(6,6,6-trifluorohexyl)thien-2-yl}-ethyl]urea m.p. 119°-120° C. (ether-petroleum ether (40°-60° C.)).

The following formulations illustrate the invention.

EXAMPLE 19

Soft Gelatin Capsule

Each soft gelatin capsule contains:

| Active ingredient | 150 mg |
| Arachis oil | 150 mg |

After mixing together, the blend is filled into soft gelatine capsules using the appropriate equipment.

EXAMPLE 20

Hard Gelatin Capsule

Each capsule contains:

| | |
|---|---|
| Active ingredient | 50 mg |
| PEG 4000 | 250 mg |

The PEG 4000 is melted and mixed with the active ingredient. Whilst still molten, the mixture is filled into capsule shells and allowed to cool.

EXAMPLE 21

Aerosol

| | |
|---|---|
| Active ingredient | 10 mg |
| Ethanol | 50 mg |
| Dichlorodifluoromethane (Propellant 12) | 658 mg |
| Dichlorotetrafluorothane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5–1 mg active ingredient.

We claim:
1. A compound of the formula

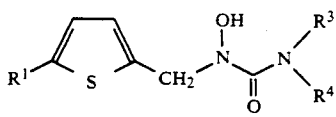

in which $R^1$ is phenylthio substituted with 1 to 3 substituents selected from halogen, nitro, cyano, carboxy, $C_{1-4}$ alkyl, $C_{1-1}$ alkylthio, halosubstituted $C_{1-4}$ alkyl and $C_{2-5}$ alkoxycarbonyl, and $R^3$ and $R^4$ are each hydrogen or $C_{1-4}$ alkyl; and salts thereof.

2. A compound according to claim 1, in which $R^1$ is phenylthio substituted with a single substituent selected from halogen, trifluoromethyl, $C_{1-4}$ alkoxy or $C_{1-4}$ alkyl.

3. A pharmaceutical formulation comprising a compound according to claim 1 or a pharmaceutically-acceptable salt thereof, together with a pharmaceutically-acceptable diluent or carrier therefor.

4. A method of treating an animal, including a human, suffering from or susceptible to leuratriene mediated disease, which comprises administering an effective amount of a compound according to claim 1, or a pharmaceutically-acceptable salt thereof.

* * * * *